United States Patent [19]
Terry

[11] 4,175,442
[45] Nov. 27, 1979

[54] METHOD AND APPARATUS FOR THE ULTRASONIC DETECTION OF FLAWS IN HOT METALLIC OBJECTS

[75] Inventor: Hazle B. Terry, Birmingham, Ala.

[73] Assignee: United States Steel Corporation, Pittsburgh, Pa.

[21] Appl. No.: 867,059

[22] Filed: Jan. 5, 1978

[51] Int. Cl.² ............................................ G01N 29/04
[52] U.S. Cl. ...................................... 73/627; 73/644
[58] Field of Search ................. 73/617, 620, 622, 627, 73/629, 632, 644, 639

[56] References Cited

U.S. PATENT DOCUMENTS

| | | | |
|---|---|---|---|
| 2,875,607 | 3/1959 | Boxcer et al. | 73/617 |
| 3,548,644 | 12/1970 | O'Connor et al. | 73/639 |
| 3,585,865 | 6/1971 | Bungart et al. | 73/644 X |
| 3,782,228 | 1/1974 | Lindemann et al. | 73/622 |
| 3,789,656 | 2/1974 | Miller | 73/644 X |

*Primary Examiner*—Charles A. Ruehl
*Attorney, Agent, or Firm*—Frank Madonia; Rea C. Helm

[57] ABSTRACT

A method and apparatus for the ultrasonic detection of pipe cavity in hot slabs, blooms, and billets to determine the optimum cropping length. An ultrasonic transducer surrounded by a water-jacket for circulating a cooling medium is embedded in a blade of the crop shear of a primary mill. The pressure of the shear blade against the workpiece is utilized to create the proper acoustic couple between the workpiece and the transducer.

2 Claims, 5 Drawing Figures

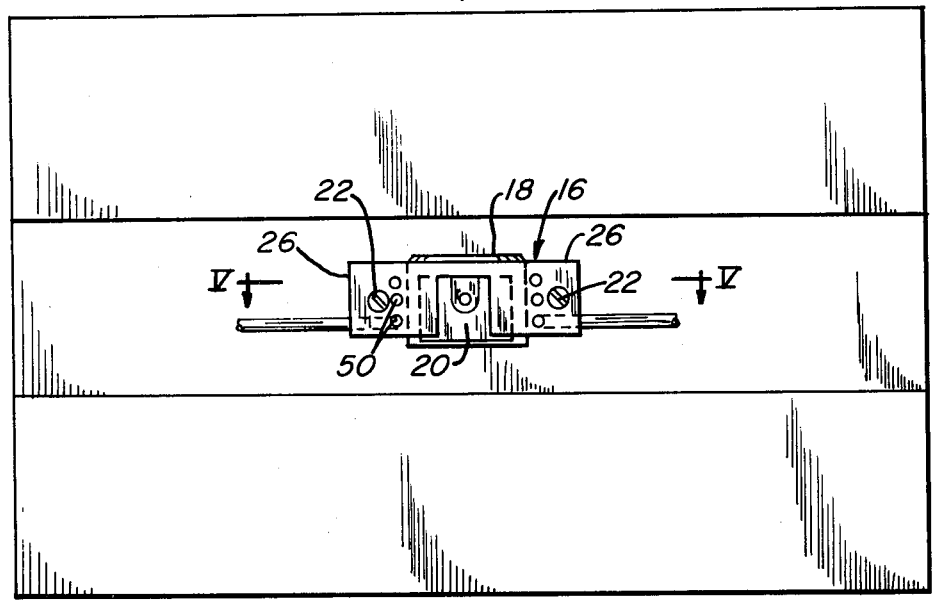
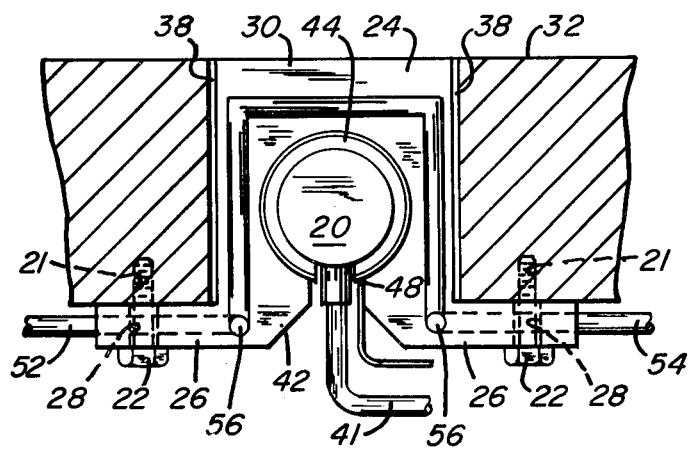
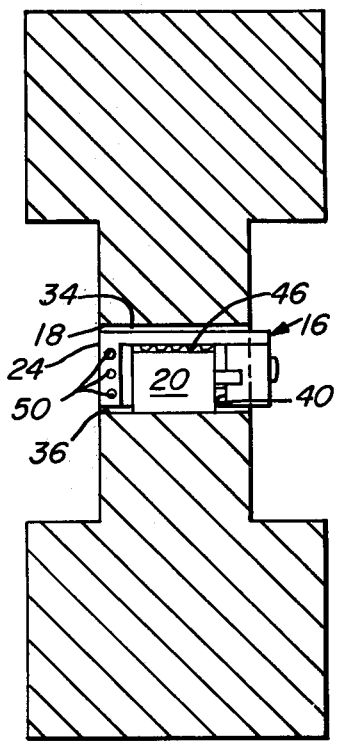

METHOD AND APPARATUS FOR THE ULTRASONIC DETECTION OF FLAWS IN HOT METALLIC OBJECTS

BACKGROUND OF THE INVENTION

In accordance with the reheating method of converting steel from ingot to bloom or slab form after stripping, ingots are charged in the soaking pits of a primary (blooming or slabbing) mill and brought to a uniform temperature of approximately 2400° F. The ingots are removed from the soaking pits and placed on the entry roll table of the primary mill, then passed along a roller table to the reducing stand which shapes the ingots into blooms or slabs. The workpiece (bloom or slab) is advanced toward a shear at the end of the mill roller table. The shear cuts the product to the designated length, cropping sufficient scrap from the two ends of the product, corresponding to what was the top and the bottom of the ingot, to insure the elimination of pipe, porosity, and other similar defects.

The problem of accurately determining the optimum cropping point in hot primary mill products has plagued the steel industry for years. The location of this optimum cropping point is in sound product just beyond the extent of primary pipe, but not into the secondary pipe. Traditionally, locating the crop point was dependent upon the experience and judgment of the crop shear operator. He would often have to shear the product more than one time before he would cut through sound product. This procedure resulted in a waste of the operator's time as well as in a reduction of product yield.

Ultrasonic transducers are commercially available that can scan a relatively cold slab, bloom or billet and reveal any internal non-homogeneous portions of the product as an acoustic couple can be easily achieved with a cold product. The use of ultrasonics in testing steel products at relatively high temperatures is not new. Others have tried ultrasonics but have encountered problems in attempting to achieve a proper acoustic couple between the workpiece and the ultrasonic transducer. Normal production temperatures of 1950° F. (1066° C.) are detrimental to transducers commercially available and therefor proper intimate contact between the product and the transducer to form the acoustic couple was thought to be impossible. Without the necessary acoustic couple an accurate determination of any flaw in the workpeice is impossible.

SUMMARY OF THE INVENTION

According to the present invention, an ultrasonic transducer is fitted with a water-jacket and then embedded in one of the blades of a crop shear. When the shear blade contacts the hot workpiece with sufficient pressure, an acoustic couple is formed between the transducer and the workpiece through the shear blade. Before a cut is made, the shear operator is able to ultrasonically "scan" the workpiece to determine the optimum cropping length for the elimination of pipe from the workpiece.

It is an object of this invention to utilize the mechanical pressure of the crop shear to achieve the acoustic couple required to reliably propagate ultrasonics through hot slabs, blooms, and billets to locate the extent of the pipe cavity and thereby the optimum cropping point.

It is another object of this invention to use the blade of the crop shear as an ultrasonic delay line to increase resolution of the pipe picture.

It is a further object of this invention to water-cool the transducer for thermal protection.

BRIEF DESCRIPTION OF THE DRAWINGS

FIG. 3 is a larger scale front elevational view of the lower shear blade of FIG. 2.

FIG. 4 is a cross-sectional view along the line IV—IV of FIG. 3.

FIG. 5 is a cross-sectional view along the line V—V of FIG. 3 and depicting the water-cooled transducer holder assembly in greater detail.

DESCRIPTION OF THE PREFERRED EMBODIMENT

Figure 1:
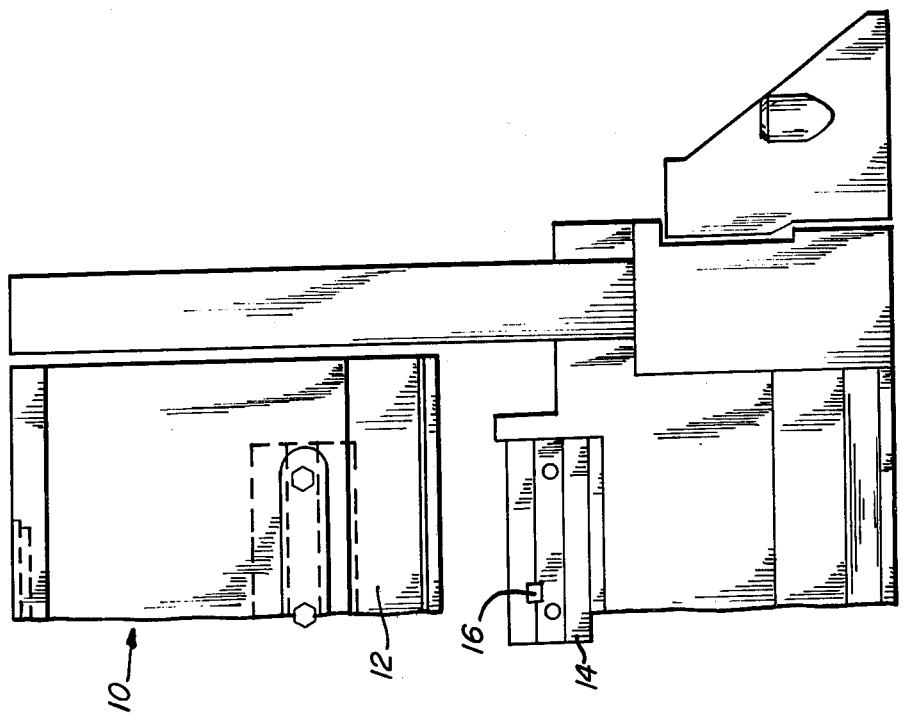
FIG. 1 is a cross-sectional side elevational view of the shear in which an ultrasonic pipe detector has been installed.
Figure 2:
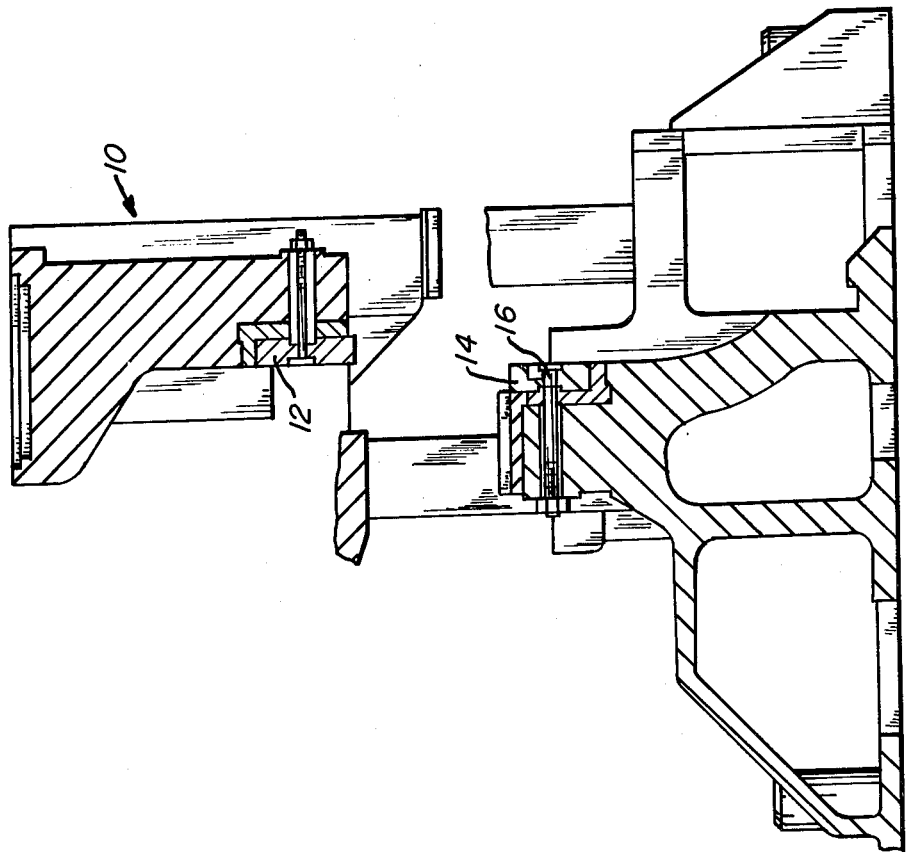
FIG. 2 is a front elevational view of the shear of FIG. 1.

With reference to FIGS. 1 and 2, the shear apparatus 10 is shown in a side cross-sectional view and a front elevational view, respectively. The shear comprises an upper blade 12 and a lower blade 14, either of which may be made to accommodate the transducer holder assembly 16. In the typical down-and-up-cut shear, the upper blade comes down to act as a gag to hold the workpiece while the lower blade moves upward to make the cut. It is preferred that in this type shear the transducer holder assembly be placed in the upper blade as the inspection for pipe may take place by merely moving the upper blade into contact with the workpiece with sufficient pressure to achieve the proper acoustic couple and then moving the lower blade to make the cut only when the optimum crop point has been found. For purposes of this description, the assembly is shown mounted in the lower shear blade.

Referring now to FIGS. 3 and 4, it may be seen that the blade has been prepared for receiving the transducer holder assembly 16 by machining a rectangular slot 18 through the blade about midway between the upper and lower surfaces and midway between the left and right sides. The slot is sufficiently large to accommodate the holder 16 in which the transducer 20 is mounted. On each side of the slot is a threaded hole 21 (FIG. 5) for receiving the mounting bolts 22.

The transducer holder assembly 16 is preferably made of a material with a high thermal conductivity such as copper or brass. It is T-shaped in cross section having a main rectangular portion 24 and a pair of opposing mounting ears 26. The mounting ears have bolt holes 28 (FIG. 5) corresponding to the threaded holes 21 in the shear blade opposite the slot 18. The rectangular portion 24 corresponds to the shape of the slot 18. When properly mounted, the holder 16 has its rear wall 30 flush with the outer surface of the rear wall 32 of the shear blade; its top 34, bottom 36 and sides 38 are in close proximity with, but do not touch, the inside walls of the slot. The bolt holes 28 in the mounting ears 26 should be large enough to allow for adjusting the holder so that it may be properly installed in the slot.

The bottom wall 36 of the holder 16 has a bore 40 in the vertical direction of a depth slightly less than the height of the transducer chosen for installation. If the transducer is to be placed in the upper blade, the bottom of the holder should be bored. If desired, the holder may be made symmetrical so that it will accommodate installation in either the upper or lower shear blade merely by inverting the holder and thus the direction of the transducer bore 40. The transducer 20 has lead cable 41 which connects the transducer to instrumentation necessary for its operation. This instrumentation is well known and therefore has not been shown in the figures. Access to the bore for the lead cable 40 from the transducer is via a slot 42 in the forward face of the holder.

Fitted into the bore 40 is a transducer adapter sleeve 44 of the split-ring type. It is the same length as the bore and fits snugly to make contact along its entire surface with the sides of the bore. The material of which the sleeve is desirably made is a metal of high thermal conductivity such as copper or brass. The transducer 20 is then fitted in sleeve 44. The forward face of the transducer is facing away from the holder 16. The sleeve is designed so that the transducer fits as snugly in the inside diameter of the sleeve as the sleeve in the bore. This tends to increase thermal conductivity through the transducer-sleeve-holder assembly.

When the transducer 20 and its sleeve 44 are fitted in the holder 16, a suitable spring 46 is placed between the holder and the bottom face of the transducer in order to urge the transducer outwardly from the holder. This outward pressure assures an acoustic couple between the forward transducer face and the shear blade when the assembly is fitted in its slot in the blade. A thermocouple 48 is attached to the sleeve in order to monitor through suitable means the skin temperature of the transducer.

The temperature of the assembly is maintained within acceptable limits by providing for cooling the holder as shown in FIG. 5. A plurality of cooling passages 50 are provided in the holder which passages are connected to inlet and exit passages 52 and 54, respectively, by a pair of manifold passages 56. Through these passages a coolant such as water or the like may be circulated.

In the operation of the invention, the transducer, embedded in the shear blade, is connected via lead cable 41 to an indicating device, such as a cathode-ray-tube (CRT), through appropriate circuitry. A strip-chart recorder may also be used, either alone or connected with the CRT. The coolant is circulated through the holder. With the transducer thus set up, the workpiece, at a temperature of approximately 2000° F., is brought into the shear. The blade with the transducer is then brought into contact with the hot workpiece and a reading is taken to determine if pipe is present at that cross-section. Pressures ranging from 25 to 49 tons have been found to provide the proper acoustic couple between the transducer and the workpiece. If pipe is found, the blade is disengaged from the workpiece, the workpiece is advanced, the blade reengaged, and another reading is taken. This process is repeated until sound product is observed, at which time the workpiece is cropped.

The portion of the blade between the transducer and the hot workpiece has a three-fold purpose: (1) it acts as a pressure contact with the workpiece, (2) it offers mechanical and thermal protection for the transducer, and (3) it provides an ultrasonic delay line to improve resolution of the ultrasonic reading. With a distance of five inches between the transducer and the workpiece and with approximately 40 tons of pressure applied to the workpiece, an instrument gain setting of 40 db offers a favorable display signal on the CRT with a minimum of objectionable noise from grain structure or blade configuration at the point of contact.

From the foregoing, it is seen that the ultrasonic detection of the optimum crop point in hot metal workpieces may be accomplished by embedding in a blade of the crop shear a transducer in a holder having passages for the circulation of a coolant medium.

Various changes may be made in the preferred embodiment of the invention hereinabove set forth and, therefore, it is to be understood that this embodiment is meant to be merely illustrative of and not to limit the invention as defined in the following claims.

We claim:

1. A method of determining the optimum crop point of a hot rolled primary mill product, said method comprising:
   (1) positioning said mill product with one end thereof between the upper and lower blades of a crop shear, one blade of said crop shear having acoustically coupled therewith an ultrasonic transducer connected to an indicating device,
   (2) contacting respectively, the upper and lower surfaces of said product end with the upper and lower blades of the shear and with sufficient pressure to form an acoustic couple between said transducer and said product, and
   (3) monitoring the indicating device to determine if a primary pipe is in the plane of said crop shear blades.

2. In a shear for removing imperfect portions of a hot metallic workpiece, said shear having a pair of oppositely displaced shear blades for engaging said workpiece, the improvement comprising:
   an ultrasonic transducer and operating means connected therewith; said transducer mounted in one of said shear blades with pressure to provide acoustic coupling thereto and directed so that when said shear blade in which said transducer is mounted contacts said workpiece, an acoustic couple is produced between said transducer and said workpiece through said shear blade lying therebetween whereby imperfections may be detected.

* * * * *